(12) United States Patent
During

(10) Patent No.: US 9,682,069 B2
(45) Date of Patent: *Jun. 20, 2017

(54) METHODS OF TREATING DRAVET SYNDROME

(71) Applicant: Ovid Therapeutics Inc., New York, NY (US)

(72) Inventor: Matthew During, Weston, CT (US)

(73) Assignee: OVID THERAPEUTICS INC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/191,068

(22) Filed: Jun. 23, 2016

(65) Prior Publication Data

US 2017/0014392 A1     Jan. 19, 2017

Related U.S. Application Data

(60) Provisional application No. 62/193,717, filed on Jul. 17, 2015, provisional application No. 62/207,595, filed on Aug. 20, 2015, provisional application No. 62/215,831, filed on Sep. 9, 2015, provisional application No. 62/332,567, filed on May 6, 2016.

(51) Int. Cl.
| | |
|---|---|
| *A01N 43/00* | (2006.01) |
| *A01N 43/46* | (2006.01) |
| *A61K 31/55* | (2006.01) |
| *A61K 31/437* | (2006.01) |
| *A61K 9/00* | (2006.01) |
| *A61K 45/06* | (2006.01) |

(52) U.S. Cl.
CPC .......... *A61K 31/437* (2013.01); *A61K 9/0053* (2013.01); *A61K 45/06* (2013.01)

(58) Field of Classification Search
USPC .......................................................... 514/217
See application file for complete search history.

(56) References Cited

U.S. PATENT DOCUMENTS

| | | | |
|---|---|---|---|
| 4,278,676 A | 7/1981 | Krogsgaard-LarsenPovl | |
| 4,353,910 A | 10/1982 | Perregaard | |
| 4,362,731 A | 12/1982 | Hill | |
| 5,948,433 A | 9/1999 | Burton et al. | |
| 5,985,311 A | 11/1999 | Cordes et al. | |
| 6,461,644 B1 | 10/2002 | Jackson et al. | |
| 6,676,961 B1 | 1/2004 | Lichter | |
| 9,339,495 B2 | 5/2016 | During | |
| 9,351,968 B1 | 5/2016 | During | |
| 9,399,034 B1 | 7/2016 | During et al. | |
| 2010/0286762 A1* | 11/2010 | Gourdie | A61K 9/0024 623/1.42 |
| 2011/0046090 A1 | 2/2011 | Barlow et al. | |
| 2013/0251671 A1* | 9/2013 | Kaufman | A61K 31/197 424/85.2 |
| 2015/0352085 A1 | 12/2015 | During | |
| 2016/0228418 A1 | 8/2016 | During | |

FOREIGN PATENT DOCUMENTS

| | | |
|---|---|---|
| EP | 0000338 A2 | 1/1979 |
| WO | 9702813 A1 | 1/1997 |
| WO | 2005094820 A1 | 10/2005 |

OTHER PUBLICATIONS

Oakley et. al. (J. Pharamcol. Exp. Ther. (2013) 345:215-224).*
Lo Coco et al., "Sleep-Wake Problems in Patients with Amyotrophic Lateral Sclerosis: Implications for Patient Management," Neurodegen. Dis. Manage, vol. 2, No. 3, (2012); pp. 315-324.
Lundahl et al., "Short-term Treatment with Gaboxadol Improves Sleep Maintenance and Enhances Slow Wave Sleep in Adult Patients with Primary Insomnia," Psychopharmacology, vol. 195, (2007); pp. 139-146.
Mackenzie et al., "TDP-43 and FUS in Amyotrophic Lateral Sclerosis and Frontotemporal Dementia," Lancet Neurology, vol. 9; (Oct. 2010); pp. 995-1007.
Marshall et al., "Specific Psychiatric Manifestations Among Preclinical Huntington Disease," JAMA Neurology, vol. 64, No. 1, (Jan. 2007), Arch Neurol. 64(1) (2007); pp. 116-121; (10 pages).
Mathias et al., "The GABAA Agonist Gaboxadol Improves the Quality of Post-Nap Sleep," Psychopharmacology, vol. 157 (2001); pp. 299-304.
Mathias et al., "Effect of Repeated Gaboxadol Administration on Night Sleep and Next-Day Performance in Healthy Elderly Subjects," Neuropsychopharmacology, vol. 30, (2005) pp. 833-841.
Morton, "HDBuzz Special Feature: Huntington's Disease and Sleep," HDBuzz, Huntington's Disease Research News, Feb. 6, 2013; 8 pages.
Natural Patterns of Sleep—Healthy Sleep—http://healthysleep.med.harvard.edu/healthy/science/what/sleep-pat- terns-rem-nrem (2007); 3 pages.
Olmos-Serrano et al, "The GABAA Receptor Agonist THIP Ameliorates Specific Behavioral Deficits in the Mouse Model of Fragile X Syndorme," Developmental Neuroscience, vol. 33, Fragile X Syndrome/Review, (2011), pp. 395-403.
Pathan et al, "Chemical Penetration Enhancers for Transdermal Drug Delivery Systems," Tropical Journal of Pharmaceutical Research, vol. 8, No. 2 (2009); pp. 173-179.
Rosenberg et al, "Neuropsychological Characteristics of Huntington's Disease Carriers: A Double Blind Study," J Med Genet, vol. 32; (1995); pp. 600-604.
Rowland et al, "Amyotrophic Lateral Sclerosis," The New England Journal of Medicine, vol. 344, No. 22, May 31, 2001; pp. 1688-1700.
R. Shiwach, "Psychopathology in Huntington's Disease Patients," Acta Psychiatrica Scaninavia; vol. 90, (1994); pp. 241-246.
Tropea et al., "Partial Reversal of Rett Syndrome-like Symptoms in MeCP2 Mutant Mice," PNAS, vol. 106, No. 6, Feb. 10, 2009; pp. 2029-2034.

(Continued)

*Primary Examiner* — Marcos Sznaidman
(74) *Attorney, Agent, or Firm* — Carter, DeLuca, Farrell & Schmidt, LLP

(57) ABSTRACT

Methods of treating a developmental disorder such as Dravet syndrome by administering a pharmaceutical composition of gaboxadol or a pharmaceutically acceptable salt thereof are provided.

7 Claims, 2 Drawing Sheets

(56) References Cited

OTHER PUBLICATIONS

Videnovic et al.., "Circadian Melatoni Rhythm and Excessive Daytime Sleepiness in Parkinson Disease Free," JAMA Neurol. 71(4), 2014; Original Investigation—Apr. 2014; pp. 463-469 (12 pages).
Waldemar et al., "Recommendations for the Diagnosis and Management of Alzheimer's Disease and other Disorders Associated with Dementia: EFNS Guideline," European Journal of Neurology, vol. 14, (2007); pp. e1-e26.
Francis O Walker, "Huntington's Disease", Seminar, Lancet, vol. 369, (Jan. 20, 2007); pp. 218-228.
U.S. Appl. No. 15/209,862, filed Jul. 14, 2016 to Matthew During.
Vardya et al., "Positive Modulation of ?-Subunit Containing GABAA Receptors in Mouse neurons" Neuropharmacology, vol. 63; 2012; pp. 469-479.
U.S. Appl. No. 15/147,429, filed May 5, 2016 to Matthew During.
U.S. Appl. No. 15/185,650, filed Jun. 17, 2016 to Matthew During.
Chen et al., "A Sutdy of Central Nervous System Stimulants," J. Pharmacology Experimental Therapeutics, , vol. 123, Mar. 17, 1958; pp. 212-215.
GuideChem, CAS Database Listed 7-2-Piperidinemethanol, a,a-diphenyl-, hydroshloride (1:1), Aug. 28, 2009; pp. 1-2 (http://www.guidechem.com/dictionary/71-78-3.html).
Howard D. Fabing, "Clinical Experience with Meratran (A New Central Nervous System Stimmulant)", Diseases of the Nervous System, vol. XVI, No. 1, Jan. 1955; pp. 10-15.
Rickels et al., "Pipradrol in Mild Depression: A Controlled Study", The Journal of Clinical Pharmacology, Feb.-Mar. 1974, pp. 127-133.
White, et al, "Pipradrol and Pipradrol Derivatives", Novel Psychoactive Substances, Elsevier, 2013, Chapter 10; pp. 233-259.
Kistner et al., "Use of Pipradrol in Obstetrics and Gynecology", The New England Journal of Medicine, vol. 254, No. 11, Mar. 15, 1956; pp. 507-510.
Leon Oettinger, Jr., M.D. "Meratran—Preliminary Report of a New Drug for the Treatment of Behavior Disorders in children", Diseases of the Nervous System, Oct. 1955; pp. 299-302.
Cheng et al., "Inducing Anesthesia with a GABA Analog, THIP,", Anesthesiology, vol. 63, No. 2, Aug. 1985; pp. 147-151.
Ebert et al., "Treating Insomnia: Current and Investigational Pharmacological Approaches," Pharmacology & Therapeutics, vol. 112, 2006; pp. 612-629.
McCaffery et al., Pain: Clin. Manual (1996), pp. 1-10.
Sessler et al., Semin. Respir. Crit. Care Med. (2013), vol. 34(2), pp. 169-178.
Walsh et al. "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.
Stephanie Saul, "Merck Cancels Work on a New Insomnia Medication," The New York Times, Business Day, Mar. 29, 2007; http://www.nytimes.com/2007/03/29/business/29sleep.html?.sub.-r=0; 3 pages.
Hughes et al., "Sedation in the Intensive Care Setting," Clinical Pharmacology: Advances and Applications, (Dovepress) vol. 4, 2012; pp. 53-63.
Ransdell Pierson, "UPDATE 2-Merck, Lundbeck scrap insomnia drug after trials," Rueters, (Dow Jones); 2015; 2 pages.
Egawa et al., Decreased Tonic Inhibition in Cerebellar Granule Cells Causes Motor Dysfunction in a Mouse MOdel of Angelman Syndrome, Neurodegenerative Disease, Science Translational Medicine, vol. 4, Issue 165 (163ra157), Dec. 5, 2012. pp. 1-10.
James K. Walsh, Ph.D., "Enhancement of Slow Wave Sleep: Implications for Insomnia," Journal of Clinical Sleep Medicine, Supplement to vol. 5, No. 2, (2009); pp. 827-832.
Wang et al., "Neurobiology of Disease—The Melatonin MT1 Receptor Axis Modulates Mutant Huntingin-Mediated Toxicity," The Journal of Neuroscience, vol. 31, No. 41, Oct. 12, 2011; pp. 14496-14507.
Williams et al., "Conference Report—Angelman Syndrome 2005: Updated Consensus for Diagnostic Criteria," American Journal of Medical Genetics, vol. 140A,, 2006; pp. 413-418.
de Die-Smulders et al., "Reproductive Options for Prospective Parents in Families with Huntington's Disease: Clinical, Psychological and Ethical Reflections," Human Reproduction Update, vol. 19, No. 3, (2013); pp. 304-315.
Braat et al., "Fragile X Syndrome Neurobiology Translates Into Rational Therapy," Drug Discovery Today, vol. 00, No. 70, Feb. 2014; pp. 1-10.
International Search Report and Written Opinion of the International Searching Authority, dated Aug. 26, 2015, corresponding to International Application No. PCT/US15/34018; 12 total pages.
Olmos-Serrano et al, "Defective GABAergic Neurotransmission and Pharmacological Rescue of Neuronal Hyperexcitability in the Amygdala in a Mouse Model of Fragile X Syndrome," The Journal of Neuroscience, vol. 30, No. 29, Jul. 21, 2010; pp. 9929-9938 (25 pages).
Walter Alexander, "Sleep: Gaboxadol Enhances Slow Wave Sleep," Perelman, School of Medicine, Jun. 22, 2006; 3 pages.
Bamford et al., "A Prospective Evaluation of Cognitive Decline in Early Huntington's Disease: Functional and Radiographic Correlates," Neuroglogy, vol. 45, Oct. 1995; pp. 1867-1873.
Brooks et al., "El Escorial Revisited: Revised Criteria for the Diagnosis of Amyotrophic Lateral Sclerosis", ALS and other Motor Neuron Disorders, vol. 1, 2000; pp. 293-299.
Brown et al., "Microarray Identification of FMRP—Associated Brain mRNAs and Altered mRNA Translational Profiles in Fragile X Syndrome," Cell, vol. 107, Nov. 16, 2001; pp. 477-487.
Brown et al., "Pharmacological Characterization of a Novel Cell Line Expressing Human ?4?3? GABAA Receptors," British Journal of Pharmacology, vol. 136, No. 7, 2002; pp. 965-974.
Castrillo-Viguera et al., "Clinical Significance in the Change of Decline in ALSFRS-R,", Amyotrophic Lateral Scelerosis, vol. 11, informa healthcare, 2010; pp. 178-180.
Sarah DeWeerdt, "Fragile X Mice Show Brain-Wave Abnormalities During Sleep," SFARI, Simons Foundation, Autism Research Initiative, Jan. 25, 2013; 2 pages.
Deacon et al., "Effect of Short-Term Treatment with Gaboxadol on Sleep Maintenance and Initiation in Patients with Primary Insomnia," Sleep, vol. 30, No. 3, 2007; pp. 281-287.
Duyao et al., "Trinucleotide Repeat Length Instability and Age of Onset in Huntington's Disease," Nature Genetics, vol. 4, Nature Publishing Group, http://www.nature.com/naturegenetics; Aug. 1993; pp. 387-392.
Faulhaber et al., "The GABAA Agonist THIP Produces Slow Wave Sleep and Reduces Spindling Activity in NREM Sleep in Humans," Psychopharmacology, vol. 130, 1997; pp. 285-291.
Fox et al., "Transdermal Drug Delivery Enhancement by Compounds of Natural Origin," Molecules, vol. 16, 2011; pp. 10507-10540.
Gaboxadol, from Wikipedia, the free encylopedia,http://en.wikipedia.org/wiki/Gaboxadol, 2014; 2 pages.
Gaboxadol, Investigational Agent—Drug Development Technology, http//www.drugdevelopment-technology.com/projects/gaboxadol-2014; 3 pages.
Gaboxadol, Bluelight, http://www.bluelight.org/vb/threads/370965-Gaboxadol—(2014); 1 page.
Glykys et al., "The Main Source of Ambient GABA Responsible for Tonic Inhibition in the Mouse Hippocampus," J Physiol, vol. 582, No. 3, 2007; pp. 1163-1178.
Paul H. Gordon, "Amyotrophic Lateral Sclerosis: An Update for 2013 Clinical Features, Pathophysiology, management and Therapeutic Trials," Aging and Disease, vol. 4, No. 5, Oct. 2013; pp. 295-310.
Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.
Huntington Study Group, "Unified Huntington's Disease Rating Scale: Reliability and Consistency," Movement Disorders, vol. 11, No. 2, 1996; pp. 136-142.

(56) References Cited

OTHER PUBLICATIONS

Iber et al., "The AASM Manual for the Scoring of Sleep and Associated Events," American Academy of Sleep Medicine (2007); pp. 3-59 (57 pages).
J. Jankovic, "Parkinson's Disease: Clinical Features and Diagnosis," J. Neurol Neurosurg. Psychiatry, vol. 79, (2008); pp. 368-376.
Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.
Jonas et al., "Neural Inhibition,", Scholarpedia—http://www.scholarpedia.org/article/Neural.sub.-inhibition—(2014); 10 pages.
Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.
Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.
Marike Lancel, "Role of GABAA Receptors in the Regulation of Sleep: Initial Sleep Responses to Peripherally Administered Modulators and Agonists," Sleep, vol. 22, No. 1, (1999); pp. 33-42.
Lancel et al., "Effect of the GABAA Agonist Gaboxadol on Nocturnal Sleep and Hormone Secretion in Healthy Elderly Subjects," Am J. Physiol Endoctrinol Metab, vol. 281; (2001), pp. E130-E137.
Larsen et al.,—Research Paper—"Intestinal Gaboxadol Absorption via PAT1 (SLC36A1): Modified Absorption in vivo Following Co-administration of L-tryptophan," British Journal of Pharmacology (BJP), vol. 157, (2009); pp. 1380-1389.

* cited by examiner

METHODS OF TREATING DRAVET SYNDROME

CROSS-REFERENCE TO RELATED APPLICATIONS

This application claims the benefit of and priority to U.S. Provisional Application Ser. Nos. 62/207,595, filed Aug. 20, 2015, 62/215,831, filed on Sep. 9, 2015, and 62/332,567, filed on May 6, 2016, the entire contents of each of which are herein incorporated by reference in their entireties.

TECHNICAL FIELD

Methods of using a composition including gaboxadol or a pharmaceutically acceptable salt thereof for the treatment of developmental disorders in a subject in need thereof.

BACKGROUND

Gaboxadol (4,5,6,7-tetrahydroisoxazolo [5,4-c]pyridine-3-ol) (THIP)) is described in EP Patent No. 0000338 and in EP Patent No. 0840601, U.S. Pat. Nos. 4,278,676, 4,362,731, 4,353,910, and WO 2005/094820. Gaboxadol is a selective $GABA_A$ receptor agonist with a preference for δ-subunit containing $GABA_A$ receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia. The development was discontinued after the compound failed to show significant effects in sleep onset and sleep maintenance in a three-month efficacy study. Additionally, patients with a history of drug abuse who received gaboxadol experienced a steep increase in psychiatric adverse events.

Pipradrol is a mild central nervous system stimulant that acts on both dopamine and norepinephrine reuptake. It was originally marketed as Meratran® (Wm. S. Merrell Co of Cincinnati Ohio) and also in combination with several vitamins as Alertonic® Elixir. Pipradrol was considered an "energetic" when it first came to market in the mid to late 1950's and used for obesity, narcolepsy, and depression. Pipradrol has also been used in the setting of obstetric and gynecological practice, with multiple benefits, for example improving nausea and vomiting, premenstrual symptoms, post-partum psychosis, and menopausal-associated depression Kistner and Duncan, *The New England Journal of Medicine* 254, 507-510 (1956).

There is limited evidence that suggests pipradrol may have some efficacy in behavioral disorders in children. Oettinger, *Diseases of the Nervous System* 16, 299-302 (1955). The report concludes that the action of pipradrol lies in increasing the attention span and decreasing irritability with a resultant increase in function. However, pipradrol has been associated with side effects such as anxiety and alertness at bedtime. Fabing, *Diseases of the Nervous System* 10-15 (January 1955). In addition, although some anticonvulsant activity has been suggested, high doses of pipradrol may cause incoordinated activity and ataxia, followed by tremors and clonic convulsions. Following the Kefauver-Harris amendments to the FDA act in 1962, pipradrol was one of thousands of drugs that were assessed by special committees to define whether there was sufficient safety and efficacy to remain an approved drug. This process was called the Drug Efficacy Study Initiative or DESI. The committee which reviewed pipradrol included the psychiatrist Karl Rickels, who had published a study on 111 individuals with depression, in which pipradrol was not superior to placebo (Rickels et al., *The Journal of Clinical Pharmacology* 14, 127-133; 1974). As a result, pipradrol was removed from the FDA register of approved drugs.

There remains a need for improved methods of treating developmental disorders including Scn1a-related disorders such as Dravet syndrome.

SUMMARY

In embodiments, methods are provided for treatment of developmental disorders including epilepsy, Landau-Kleffner Syndrome, Lennox-Gastaut syndrome (LGS) and Dravet syndrome by administering to a patient in need thereof a pharmaceutical composition of gaboxadol or a pharmaceutically acceptable salt thereof.

In embodiments, methods of treating Dravet syndrome described herein include administering to a patient in need thereof a pharmaceutical composition comprising 0.1 mg to 50 mg gaboxadol or a pharmaceutically acceptable salt thereof. In embodiments, methods of treating Dravet syndrome described herein include administering to a patient diagnosed with Dravet syndrome a pharmaceutical composition comprising 0.1 mg to 50 mg gaboxadol or a pharmaceutically acceptable salt thereof.

In embodiments, methods are provided for treatment of developmental disorders including benign rolandic epilepsy (BRE), intractable childhood epilepsy (ICE), childhood absence epilepsy (CAE), juvenile myoclonic epilepsy (JME), infantile spasms (or West syndrome), Dravet syndrome and Lennox-Gastaut syndrome (LGS) by administering to a patient in need thereof a pharmaceutical composition of gaboxadol or a pharmaceutically acceptable salt thereof.

In embodiments, methods are provided for treatment of developmental disorders characterized as a sodium channel protein type 1 subunit alpha (Scn1a)-related disorder. For example, Scn1a-related disorders include generalized epilepsy with fibril seizures plus, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy and seizures by administering to a patient in need thereof a pharmaceutical composition of gaboxadol or a pharmaceutically acceptable salt thereof.

The methods described herein may be particularly effective in subjects experiencing intractable seizures, status epilepticus, akinetic seizures, myoclonic seizures, absence seizures, or severe myoclonic epilepsy in infancy (SMEI).

In embodiments, gaboxadol or a pharmaceutically acceptable salt thereof is administered to a patient diagnosed with a developmental disorder such as Dravet syndrome in a daily dosage range of about 0.05 mg to about 50 mg.

In embodiments, gaboxadol or a pharmaceutically acceptable salt thereof is co-administered with one or more of the following drugs: pipradrol, acetazolamide, carbamazepine, clobazam, clonazepam, eslicarbazepine acetate, ethosuximide, gabapentin, lacosamide, lamotrigine, leviteracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide

DETAILED DESCRIPTION

Figure 1:
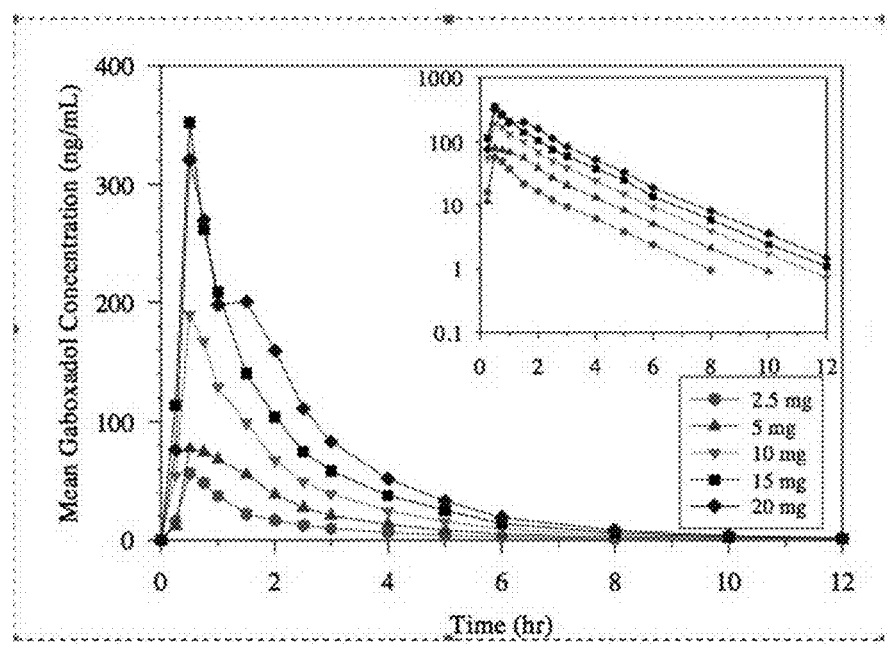
FIG. 1 shows the arithmetic mean plasma concentration-time profiles of gaboxadol following single oral doses (2.5, 5, 10, 15, and 20 mg) as described in Example 1.

Described herein are methods of treating developmental disorders such as sodium channel protein type 1 subunit alpha (Scn1a)-related disorders including Dravet syndrome with gaboxadol or a pharmaceutically acceptable salt thereof. Although up to about 80% of Dravet syndrome cases may test positive for an SCN1A gene mutation, the absence of an SCN1A mutation does not exclude Dravet syndrome diagnosis. Accordingly, in embodiments, methods described herein are directed to treating Dravet syndrome with gaboxadol or a pharmaceutically acceptable salt thereof whether or not the Dravet syndrome diagnosis is associated with an SCN1A mutation.

Many pharmaceutical products are administered as a fixed dose, at regular intervals, to achieve therapeutic efficacy. Its duration of action is reflected by its plasma half-life. Gaboxadol is a selective $GABA_A$ receptor agonist with a relatively short half-life ($t_{1/2}=2=1.5$ h). Since efficacy is often dependent on sufficient exposure within the central nervous system administration of CNS drugs with a short half-life may require frequent maintenance dosing. Advantageously disclosed herein are methods of treating development disorders by administration of gaboxadol or a pharmaceutically acceptable salt thereof. For example, in embodiments, methods of treating a developmental disorder are provided which include administering to a patient in need thereof a pharmaceutical composition including about 0.05 mg to about 50 mg gaboxadol or a pharmaceutically acceptable salt thereof wherein the composition provides improvement for more than 6 hours after administration to the patient.

Also provided herein are methods and compositions for treating developmental disorders by administering to a patient in need thereof a pharmaceutical composition comprising pipradrol, a derivative thereof, or a pharmaceutically acceptable salt thereof. In embodiments, the methods and compositions described herein include pipradrol or a pharmaceutically acceptable salt thereof.

Also provided herein are methods and compositions for treating developmental disorders by co-administering to a patient in need thereof gaboxadol or a pharmaceutically acceptable salt thereof, and pipradrol, a derivative thereof, or a pharmaceutically acceptable salt thereof. In embodiments, the methods and compositions described herein include a dosage form including gaboxadol or a pharmaceutically acceptable salt thereof, and pipradrol or a pharmaceutically acceptable salt thereof.

In embodiments, the methods described herein may be used to treat developmental disorders including epilepsy, Landau-Kleffner Syndrome, Lennox-Gastaut syndrome (LGS) and Dravet syndrome. In embodiments, the methods include treatment of Dravet syndrome.

In embodiments, the methods described herein may be used to treat developmental disorders including benign rolandic epilepsy (BRE), intractable childhood epilepsy (ICE), childhood absence epilepsy (CAE), juvenile myoclonic epilepsy (JME), infantile spasms (or West syndrome), generalized epilepsy with febrile seizure plus (GEFS+) and Lennox-Gastaut syndrome (LGS).

In embodiments, the methods described herein may be used to treat developmental disorders characterized as a sodium channel protein type 1 subunit alpha (Scn1A)-related disorder. For example Scn1A-related disorders include generalized epilepsy with fibril seizures plus, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy and seizures.

The methods described herein may be effective in subjects experiencing intractable seizures, status epilepticus, akinetic seizures, myoclonic seizures, absence seizures, or severe myoclonic epilepsy in infancy (SMEI). In embodiments, the disorders are characterized by intractable seizures. Intractable seizures (also referred to as "uncontrolled" or "refractory" seizures) are seizures that cannot be controlled with conventional treatments. For example, the subject can have intractable epilepsy or another disorder characterized by intractable seizures, or a disorder characterized by status epilepticus. Status epilepticus is a condition in which seizures follow one another without recovery of consciousness between them. Accordingly, in embodiments, the disclosed methods are used to treat subjects that are resistant to one or more conventional therapies.

The methods described herein may be particularly useful for treating children and infants, and for treating disorders that onset during infancy or childhood. In embodiments, the subject of the disclosed method is a newborn, a baby, a toddler, a preschooler, a school-age child, a tween, or a teenager. In embodiments, the subject is 18 years old or younger, 12 years old or younger, 10 years old or younger, 8 years old or younger, 6 years old or younger, 4 years old or younger, 2 years old or younger, 1 year old or younger. In embodiments, the subject is an adult that is over eighteen years old.

In embodiments, the developmental disorders are characterized by seizures associated with epilepsy. In embodiments, the seizures are non-epileptic seizures (NES) or dissociative seizures that are distinguished from epilepsy. Non-epileptic seizures include organic non-epileptic seizures and psychogenic seizures.

Epilepsy is a neurological disorder that occurs when nerve cell activity in the brain becomes disrupted, leading to seizures or periods of unusual behavior, sensations and sometimes loss of consciousness. A subject can be said to have epilepsy when having two seizures without an obvious cause. Epilepsy can occur in both adults and children, and can be associated with a specific syndrome. Accordingly, in embodiments, the subject has a childhood epilepsy syndrome such as benign rolandic epilepsy (BRE), childhood absence epilepsy (CAE), juvenile myoclonic epilepsy (JME), infantile spasms (or West syndrome), Dravet syndrome or Lennox-Gastaut syndrome (LGS).

In embodiments, the subject does not experience diagnosable seizures, but exhibits subclinical electrical discharges, which refers to a high rate of seizure-like activity when their brain waves are measured with an electroencephalogram. Epileptic syndromes associated with these seizure-like discharges include Landau-Kleffner Syndrome, Dravet syndrome and Continuous Spike-wave Activity during Slow-wave Sleep.

In embodiments, the developmental disorders treated by the methods and compositions described herein include Scn1A-related seizure disorders. Scn1A-related seizure disorders include simple febrile seizures (FS) and generalized epilepsy with febrile seizures plus (GEFS+) at the mild end to Dravet syndrome and intractable childhood epilepsy with generalized tonic-clonic seizures (ICE-GTC) at the severe end. Specific Scn1A-related seizure disorders include, but are not limited to, generalized epilepsy with fibril seizures plus, intractable childhood epilepsy with generalized tonic-clonic seizures, intractable infantile partial seizures, myoclonic-astatic epilepsy, severe myoclonic epilepsy in infancy, simple febrile seizures, Dravet syndrome, Lennox-Gastaut syndrome (LGS), infantile spasms, and vaccine-related encephalopathy.

In embodiments, the subject has an intellectual developmental disability (IDD) such as an Autism Spectrum Disorders (ASD). In embodiments, the subject of the disclosed method has epilepsy and an IDD or ASD disorder. Common IDD and ASD that are comorbid with seizures and epilepsy include, but are not limited to, fragile X syndrome (FXS), Rett syndrome (RTT), Angelman syndrome, Prader-Willi syndrome, Velocardiofacial syndrome, Smith-Lemli-Opitz syndrome, neuroligin mutations and "interneuronopathies" resulting from aristaless-related homeobox, X-linked (ARX) and Nueropilin 2 (NRP2) gene mutations.

Embodiments described herein provide that a patient in need thereof is administered a pharmaceutical composition including gaboxadol or a pharmaceutically acceptable salt thereof. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylene-salicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about 0.0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, methods of treating a developmental disorder such as Dravet syndrome include administering to a patient in need thereof a pharmaceutical composition including about 0.05 mg to about 50 mg gaboxadol or a pharmaceutically acceptable salt thereof. In embodiments, methods of treating a developmental disorder such as Dravet syndrome include administering to a patient in need thereof a pharmaceutical composition including about 0.1 mg to about 30 mg gaboxadol or a pharmaceutically acceptable salt thereof.

In embodiments, the pharmaceutical compositions include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

Pharmaceutical compositions herein may be provided with immediate release, delayed release, extended release, or modified release profiles. In embodiments, pharmaceutical compositions with different drug release profiles may be combined to create a two phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

In embodiments, the pharmaceutical compositions described herein are administered once, twice, or three times daily, or every other day. In embodiments, a pharmaceutical composition described herein is provided to the patient in the evening. In embodiments, a pharmaceutical composition described herein is provided to the patient once in the evening and once in the morning. In embodiments, the total amount of gaboxadol or a pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 5 mg, 10 mg, or 15 mg. In embodiments, the total amount of gaboxadol or a pharmaceutically acceptable salt thereof administered to a subject in a 24-hour period is 20 mg. In embodiments, the subject may be started at a low dose and the dosage is escalated. In this manner, it can be determined if the drug is well tolerated in the subject. Dosages can be lower for children than for adults. In embodiments, a dose of gaboxadol for children can be 0.1 mg/kg to 1 mg/kg.

In embodiments, provided herein are methods of treating a developmental disorder such as Dravet syndrome including administering to a patient in need thereof a pharmaceutical composition including gaboxadol or a pharmaceutically acceptable salt thereof wherein the composition provides improvement in at least one symptom of the developmental disorder. In embodiments, methods of treating developmental disorders by administering to a subject in need thereof an effective amount of gaboxadol or a pharmaceutically acceptable salt, derivative or analogue, or combination thereof, are provided. An effective amount or therapeutically effective amount can be a dosage sufficient to treat, inhibit, or alleviate one or more symptoms of a developmental disorder such as reducing the frequency or severity of seizures, reducing behavior abnormalities (or otherwise improving behavior); or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.).

In embodiments, the methods described herein are effective to reduce, delay, or prevent one or more other clinical symptoms of a developmental disorder, particularly epilepsy or Dravet syndrome. For example, the effect of a composition including gaboxadol or a pharmaceutically acceptable salt thereof on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

In embodiments, the methods provided may also surprisingly and unexpectedly reduce or prevent seizures, or symptoms thereof in a subject in need thereof. In embodiments, the methods provided may reduce or prevent one or more different types of seizures. Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In embodiments, methods described herein may reduce the frequency of seizures, reduce the severity of seizures, change the type of seizures (e.g., from a more severe type to a less severe type), or a combination thereof in a subject after treatment compared to the absence of treatment (e.g., before treatment), or compared to treatment with an alternative conventional treatment.

In embodiments, provided herein are methods of treating a developmental disorder including administering to a patient in need thereof a pharmaceutical composition including gaboxadol or a pharmaceutically acceptable salt thereof wherein the composition provides improvement of at least one symptom for more than 4 hours after administration of the pharmaceutical composition to the patient. In embodiments, the improvement of at least one symptom for more than 6 hours after administration of the pharmaceutical composition to the patient is provided in accordance with the present disclosure. In embodiments, improvement of at least one symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for 12 hours after administration of the pharmaceutical composition to the patient is provided in accordance with the present disclosure.

In embodiments, provided herein methods of treating a developmental disorder including administering to a patient in need thereof a pharmaceutical composition including gaboxadol or a pharmaceutically acceptable salt thereof wherein the composition provides improvement in next day functioning to the patient.

In embodiments, provided herein are methods of treating a developmental disorder wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating a developmental disorder wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating a developmental disorder wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement of next day functioning of the patient. In embodiments, the composition provides an in vivo plasma profile having a $C_{max}$ less than about, e.g., 250 ng/ml, 200 ng/ml 150 ng/ml, or 100 ng/ml and wherein the composition provides improvement of next day functioning of the patient.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng·hr/ml. In embodiments, the composition provides improvement in next day functioning of the patient. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the composition provides improvement of next day functioning of the patient. In embodiments, the composition provides improvement in one or more symptom for more than 6 hours after administration.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, wherein the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the composition provides improvement of next day functioning of the patient after administration for more than, e.g., 4 hours, 6 hours, 8 hours, 10 hours, or 12 hours, after administration of the composition to the patient.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments the first and/or the second pharmaceutical compositions are administered once, twice, or three times daily, or every other day. In embodiments, the first or the second pharmaceutical composition is provided to the patient in the evening. In embodiments, the second pharmaceutical composition includes an amount of gaboxadol that is at least one third of the amount of gaboxadol provided in the first pharmaceutical composition. In embodiments, the second pharmaceutical composition includes an amount of gaboxadol that is at least half of the amount of gaboxadol provided in the first pharmaceutical composition.

In embodiments, the first or the second pharmaceutical composition is provided to the patient once in the evening and once in the morning. In embodiments, the total amount of gaboxadol or pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 10 mg, 15 mg, or 20 mg. In embodiments, the total amount of gaboxadol or a pharmaceutically acceptable salt thereof administered to a subject in a 24-hour period is 20 mg.

In embodiments, the first and/or the second pharmaceutical compositions may be provided with immediate release, delayed release, extended release, or modified release profiles. The first and second pharmaceutical compositions may be provided at the same time or separated by an interval of time, e.g., 6 hours, 12 hours etc. In embodiments, the first and the second pharmaceutical compositions may be provided with different drug release profiles to create a two-phase release profile. For example, the first pharmaceutical composition may be provided with an immediate release profile and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In some embodiments, the first pharmaceutical composition is an immediate release composition. In embodiments, the second pharmaceutical composition is an immediate release composition. In embodiments, the first and second pharmaceutical compositions are provided as separate immediate release compositions, e.g., tablets or capsules. In embodiments the first and second pharmaceutical compositions are provided 12 hours apart.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about, e.g., 25%, 30%, 35%, 40%, 45% or 50% less than the first pharmaceutical composition. In embodiments, the composition provides improvement of next day functioning of the patient. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the patient. In embodiments, the first pharmaceutical composition provides improvement in one or more symptom for more than, e.g., 6 hours, 8 hours or 12 hours after administration of the first pharmaceutical composition.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour.

In embodiments, the first pharmaceutical composition provides a dissolution of at least about 80% within the first 20 minutes of administration to a patient in need thereof. In embodiments, the first pharmaceutical composition provides a dissolution of at least about, e.g., 85%, 90% or 95% within the first 20 minutes of administration to a patient in need thereof. In embodiments, the first pharmaceutical composition provides a dissolution of at least 80% within the first 10 minutes of administration to a patient in need thereof.

In embodiments the first and/or the second pharmaceutical compositions are sub therapeutic dosages. A sub therapeutic dosage is an amount of gaboxadol pharmaceutically acceptable salt thereof that is less than the amount required for a therapeutic effect. In embodiments, a sub therapeutic dosage is an amount of gaboxadol pharmaceutically acceptable salt thereof that alone may not provide improvement in at least one symptom of the developmental disorder but is sufficient to maintain such improvement. In embodiments, the methods provide administering a first pharmaceutical composition that provides improvement in at least one symptom of a development disorder and a second composition that maintains the improvement. In embodiments, after administration of the first pharmaceutical composition the second pharmaceutical composition may provide a synergistic effect to improve at least one symptom of a developmental disorder. In embodiments the second pharmaceutical composition may provide a synergistic effect to improve at least one symptom of a developmental disorder.

In embodiments, provided herein are methods of treating a developmental disorder including administering to a patient in need thereof a pharmaceutical composition including a first pharmaceutical dosage including gaboxadol or a pharmaceutically acceptable salt thereof wherein the composition provides improvement for more than 6 hours after administration and a second pharmaceutical composition including a sub therapeutic dosage of gaboxadol or a pharmaceutically acceptable salt thereof.

Administration of the first and second pharmaceutical compositions may be separated by an interval of time to achieve long-term improvement in at least one symptom. In embodiments, the first and second pharmaceutical composition may be administered 6 hours apart. In embodiments the first and second pharmaceutical composition may be administered 12 hours apart. In embodiments, the first and second pharmaceutical compositions may administered within, e.g., 6 hours, 12 hours, 18 hours, 24 hours etc. In embodiments, the first and second pharmaceutical compositions may administered separated by at least, e.g., 6 hours, 12 hours, 18 hours, 24 hours etc. In embodiments, improvement in at least one symptom of a developmental disorder for more than 8 hours after administration to the patient is provided. In embodiments, improvement for more than about, e.g., 10 hours, 12 hours, 15 hours, 18 hours, 20 hours, or 24 hours after administration to the patient is provided.

In embodiments, the first pharmaceutical composition and/or the second pharmaceutical composition include about 0.1 mg to about 40 mg gaboxadol or a pharmaceutically acceptable salt thereof. The amount of gaboxadol or a pharmaceutically acceptable salt thereof in the first pharmaceutical composition and the second pharmaceutical composition may be the same or different. In embodiments, the administration of the first and second pharmaceutical composition may provide a synergistic effect to improve at least one symptom of a developmental disorder.

In embodiments, the first and/or the second pharmaceutical composition include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, or 3 mg to 15 mg gaboxadol or a pharmaceutically acceptable salt thereof.

In embodiments, the first and/or the second pharmaceutical composition include 5 mg to 15 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the first and/or the second pharmaceutical composition include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the first pharmaceutical compositions include 2.5 mg, 5 mg, 7.5 mg, 10 mg, 15 mg, or 20 mg gaboxadol or a pharmaceutically acceptable salt thereof. In embodiments, the second pharmaceutical compositions include 2.5 mg, 5 mg, 7.5 mg, 10 mg, 15 mg, or 20 mg gaboxadol or a pharmaceutically acceptable salt thereof.

In embodiments, methods of treating developmental disorders include administration of gaboxadol or a pharmaceutically acceptable salt thereof in combination with one or more other active compounds. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. Thus, treatment is provided of a developmental disorder with a combination of agents that combined, may provide a synergistic effect that enhances efficacy.

In embodiments, gaboxadol or a pharmaceutically acceptable salt thereof, is administered in combination with conventional therapy for seizures, epilepsy, or one of the other disorders disclosed herein. For example, common conventional therapies for seizures and epilepsy include antiepileptic drugs and non-antiepileptic drug treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, valgus nerve stimulation, corticectomy, and multiple subpial transections.

Common antiepileptic and anticonvulsive active compounds that may be used in combination with gaboxadol or a pharmaceutically acceptable salt thereof include, but are not limited to, acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

In embodiments, methods and compositions are provided for treating developmental disorders by administering to a patient in need thereof a pharmaceutical composition comprising pipradrol or a pharmaceutically acceptable salt thereof. In embodiments, compounds structurally related to pipradrol or a derivative or analog thereof are administered. Such compounds, can include, for example, desoxypipradrol, diphenylprolinol, 2-(diphenylmethyl)pyrrolidine, or pharmaceutically acceptable salts thereof.

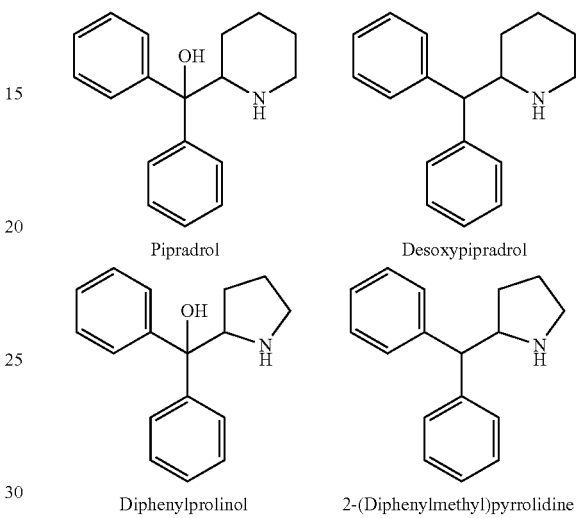

Pipradrol          Desoxypipradrol

Diphenylprolinol          2-(Diphenylmethyl)pyrrolidine

Pipradrol, derivatives, analogues and structurally related compounds thereof useful in the disclosed methods includes any form of the compounds, such as the base (zwitter ion), pharmaceutically acceptable salts, e.g., pharmaceutically acceptable acid addition salts, hydrates or solvates of the base or salt, as well as anhydrates, and also amorphous, or crystalline forms.

In embodiments, deuterated pipradrol or deuterated forms of pipradrol derivatives may be used. Deuteration of pharmaceuticals to improve pharmacokinetics (PK), pharmacodynamics (PD), and toxicity profiles, has been demonstrated previously with some classes of drugs. Accordingly the use of deuterium-enriched pipradrol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched pipradrol.

Deuterium enriched pipradrol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments, deuterium enriched pipradrol means that the specified position is enriched with deuterium above the naturally occurring distribution (i.e., above about 0.0156%). In embodiments, deuterium enrichment is, e.g., no less than about 1%, no less than about 5%, no less than about 10%, no less than about 20%, no less than about 50%, no less than about 70%, no less than about 80%, no less than about 90%, or no less than about 98% of deuterium at a specified position. In embodiments, deuterium enrichment may be defined as, e.g., more than about 60%, more than about 65%, more than about 75%, more than about 80%, more than about 85%, more than about 95% deuterium at a specified position.

In embodiments, the pipradrol or a pharmaceutically acceptable salt thereof may include the racemic mixture, as well as compositions including each enantiomer individually. The compositions and methods contemplated herein may provide reduced dosing frequency, reduced adverse events and/or increased efficacy compared to a racemic mixture of pipradrol. In embodiments, compositions and methods that include each enantiomer individually may provide reduced dosing frequency, reduced adverse events and/or increased efficacy compared to the minor enantiomer. Thus, for example, contemplated herein are compositions and methods of treatment that provide the S enantiomer of pipradrol or a pharmaceutically acceptable salt thereof that is substantially free of the R enantiomer. In embodiments, methods and compositions herein include the R enantiomer of pipradrol or a pharmaceutically acceptable salt thereof substantially free of the S enantiomer. By "substantially free" it is meant that the composition includes less than 50% of the minor enantiomer. In embodiments, the compositions and methods herein may include less than about, e.g., 25%, 15%, 10%, 8%, 5%, 3%, 2%, or less than 1% of the minor enantiomer.

In embodiments, the methods and compositions include (S)-pipradrol, or a pharmaceutically acceptable salt thereof. In embodiments, the compositions include more than, e.g., about 75%, about 85%, about 90%, about 95% or about 98% (S)-pipradrol. In embodiments, the compositions include between, e.g., about 50% to about 75%, about 75% to about 100%, about 85% to about 100%, about 90% to about 100%, or about 95% to about 100% (S)-pipradrol.

In embodiments, the methods and compositions herein include (R)-pipradrol, or a pharmaceutically acceptable salt thereof. In embodiments, the compositions include more than, e.g., about 75%, about 85%, about 90%, about 95% or about 98% (R)-pipradrol. In embodiments, the compositions include between, e.g., about 50% to about 75%, about 75% to about 100%, about 85% to about 100%, about 90% to about 100%, or about 95% to about 100% (R)-pipradrol.

In embodiments, pipradrol or a pharmaceutically acceptable salt thereof is administered at dosages ranging from about 0.001 mg/kg and about 10 mg/kg of body weight of a patient in need thereof, e.g., from about 0.01 mg/kg to 2.0 mg/kg at least once a day. For example, dosages may include amounts of pipradrol or a pharmaceutically acceptable salt thereof in the range of about, e.g., 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, and 30 mg being specific examples of doses.

Typically, dosages of pipradrol or pharmaceutically acceptable salts thereof are administered once or twice daily to a patient in need thereof. The methods and compositions described herein may provide reduced dosing frequency and reduced adverse events and/or increased efficacy. In embodiments, the dosage is about, e.g., 0.1-20 mg/day, or 0.2-15 mg/day, or 0.5-10 mg/day, or 0.75-5 mg/day, for example 0.2 mg/day, 0.5 mg/day, 0.75 mg/day, 1 mg/day, 1.5 mg/day, 2 mg/day, 3 mg/day, 4 mg/day, 5 mg/day, 6 mg/day, 7 mg/day, 8 mg/day, 9 mg/day, or 10 mg/day. In embodiments, pipradrol, or a derivative or analogue thereof is administered at doses of 0.2 mg to 1 mg in infants or 1-20 mg in adults, once daily.

Methods of treating developmental disorders by administering to a subject in need thereof an effective amount of pipradrol or a pharmaceutically acceptable salt, derivative or analogue, or combination thereof, are provided. An effective amount or therapeutically effective amount can be a dosage sufficient to treat, inhibit, or alleviate one or more symptoms of a developmental disorder such as reducing the frequency or severity of seizures, reducing behavior abnormalities (or otherwise improving behavior); or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.).

In embodiments, the methods described herein are effective to reduce, delay, or prevent one or more other clinical symptoms of a developmental disorder, particularly epilepsy or Dravet syndrome. For example, the effect of a composition including pipradrol or a pharmaceutically acceptable salt, derivative or analogue thereof on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

Pipradrol or a pharmaceutically acceptable salt, derivative or analogue thereof as described herein may be considered stimulants because they "stimulate" motor behavior. These effects may come at a cost, since, in certain instances, stimulants can increase agitation and anxiety, reduce sleep, and inhibit appetite. Moreover, many can be addictive and have abuse potential. At higher doses stimulants may induce convulsions. On the simplest level, a stimulant may be considered to be the opposite of a depressant, and depressants, such as barbiturates and benzodiazepines which may have robust anti-epileptic activity. Therefore, it is commonly believed that certain stimulants can be pro-convulsant and may typically be considered as contraindicated in the treatment of developmental disorders. Indeed, there is some clinical evidence that certain stimulants may lower the convulsive threshold in patients with prior history of seizures, in patients with prior electroencephalogram (EEG) abnormalities in the absence of seizures, and, rarely, in patients without a history of seizures and no prior EEG evidence of seizures. Accordingly, the methods and compositions described herein may surprisingly provide reduction in the frequency of seizures, the severity of seizures, or a combination thereof in a patient diagnosed with a developmental disorder.

In embodiments, compositions and methods of treatment are provided with low dosages of pipradrol such that the patient is provided one or more beneficial effects related to a developmental disorder, such as, reduced seizure activity, reduced fatigue, increased mood, increased concentration, increased behavioral control and/or increased cognitive ability. Pipradrol is known to have a relatively long half-life that may lead to prolonged effects and drug accumulation in a patient. Provided herein are dosing regimens that allow effective treatment of a developmental disorder with potentially limited or substantially few negative side effects, e.g., convulsions and/or sleep disruption. Accordingly, the methods described herein may provide treatment of a development disorder that may be considered surprising and unexpected. For example, methods are provided herein of treating developmental disorders in a patient in need thereof which may not cause sleep disruption. In embodiments, methods described herein may provide effective treatment of a development disorder without interrupting Slow Wave Sleep. In embodiments methods of treating a developmental disorder without causing insomnia or trouble falling asleep are provided.

The methods provided may also surprisingly and unexpectedly reduce or prevent seizures, or symptoms thereof in a subject in need thereof. The methods provided may reduce or prevent one or more different types of seizures. Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In embodiments, methods described herein may reduce the frequency of seizures, reduce the severity of seizures, change the type of seizures (e.g., from a more severe type to a less severe type), or a combination thereof in a subject after treatment compared to the absence of treatment (e.g., before treatment), or compared to treatment with an alternative conventional treatment.

The disclosed compounds, such as gaboxadol or pharmaceutically acceptable salts thereof, or pipradrol, pharmaceutically acceptable salts, derivatives and/or analogues thereof, can be used individually as a monotherapy as the only active agent. In embodiments, methods are provided of treating development disorders using pipradrol or a pharmaceutically acceptable salt thereof in a pharmaceutically acceptable carrier. In embodiments, methods of treating developmental disorders include administration of pipradrol, pharmaceutically acceptable salts, derivatives and/or analogues thereof in combination with one or more other active compounds. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. Thus, treatment is provided of a developmental disorder with a combination of agents that combined, may provide a synergistic effect that enhances efficacy.

In embodiments, gaboxadol or pharmaceutically acceptable salts thereof, or pipradrol, pharmaceutically acceptable salts, derivatives and/or analogues thereof, or both, is administered in combination with conventional therapy for seizures, epilepsy, or one of the other disorders disclosed herein. For example, common conventional therapies for seizures and epilepsy include antiepileptic drugs and non-antiepileptic drug treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, valgus nerve stimulation, corticetomy, and multiple subpial transections.

Common antiepileptic and anticonvulsive active compounds that may be used in combination with pipradrol include, but are not limited to, acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

In embodiments, a co-therapy of pipradrol, a pharmaceutically acceptable salt thereof, or a derivative thereof and gaboxadol or a pharmaceutically acceptable salt thereof is effective to reduce seizure frequency or severity in the subject greater than either compound is administered alone. In embodiments, the co-therapy produces a more than additive result compared to compounds administered individually.

In embodiments, the subject may be started at a low dose and the dosage is escalated. In this manner, it can be determined if the drug is well tolerated in the subject. Dosages can be lower for children than for adults.

In embodiments, such as combination therapies, a dose of gaboxadol for children can be 0.1 mg/kg to 1 mg/kg, and the dose for pipradrol may be 0.01 mg/kg to 0.1 mg/kg. The weight/weight ratio of gaboxadol and pipradrol is can be 10-to-1. However, the dosing ratio based on milligrams of active pharmaceutical ingredient (API) can range from 0.1-to-1 to 100-to-1 of gaboxadol-to-pipradrol respectively.

Effective treatment of a developmental disorder (e.g., SMEI or Dravet syndrome) herein may be established by showing reduction in the frequency of seizures (e.g., more than 50%) after a period of time compared with baseline. For example, after a baseline period of 1 month, the patients may be randomly allocated gaboxadol or pipradrol or placebo as add-on therapy to standard therapies, such as valproate and clobazam, during a double-blind period of 2 months. Primary outcome measurements may include the percentage of responders on gaboxadol or pipradrol and on placebo, defined as having experienced at least a 50% reduction of clonic (or tonic-clonic) seizure frequency during the second month of the double-blind period compared with baseline. Patients who present with status epilepticus during the double-blind period may be regarded as non-responders. Secondary outcomes may include the absolute count of clonic (or tonic-clonic) seizures during the second month of the double-blind period (normalized to 30 days, by dividing the raw count by the exact number of days of observation and multiplying by 30) and the percentage of change from baseline.

The effectiveness of gaboxadol and/or pipradrol for the treatment of a disclosed developmental disorder, e.g., associated with Dravet syndrome or Lennox-Gastaut syndrome, may be established in other controlled studies. For example, a randomized, double-blind, placebo-controlled study consisting of a 4-week baseline period followed by a 3-week titration period and 12-week maintenance period may be used in patients age 2-54 years with a current or prior diagnosis of Dravet syndrome or LGS. Multiple target maintenance doses of gaboxadol and/or pipradrol may be tested according to patient body weight and specific dosing regime. A primary efficacy measure may include the percent reduction in the weekly frequency of drop seizures (atonic, tonic, or myoclonic), also known as drop attacks, from the 4-week baseline period to 12-week maintenance period. Thus, efficacy may be measured as percentage reduction in weekly seizure (e.g., atonic, tonic, or myoclonic) frequency from baseline of, e.g., 0 to <20, 20 to <40, 40 to <60, 60 to <80, 80 to <100.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In embodiments, treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" may also refer to inhibiting the disease or condition, e.g., arresting or reducing its development or at least one clinical or subclinical symptom thereof "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "prevention" or "preventing" means to administer a composition to a subject or a system at risk for or having a predisposition for one or more symptoms caused by a disease or disorder to facilitate cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" are used herein interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods.

EXAMPLES

The Examples provided herein are included solely for augmenting the disclosure herein and should not be considered to be limiting in any respect.

Example 1

The following Example provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailability of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows: Treatment A—one 2.5 mg gaboxadol capsule and 1 matching placebo capsule; Treatment B—one 5 mg gaboxadol capsule and 1 matching placebo capsule; Treatment C—one 10 mg gaboxadol capsule and 1 matching placebo capsule; Treatment D—one 15 mg gaboxadol capsule and 1 matching placebo capsule; and Treatment E—20 mg gaboxadol (two 10 mg gaboxadol capsules). Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, $C_{max}$, $T_{max}$, apparent $t_{1/2}$, cumulative urinary excretion, renal clearance, clearance, and steady-state volume of distribution, as appropriate). AUC and $C_{max}$ for gaboxadol were potency adjusted to facilitate comparison of pharmacokinetic data across studies. Table 1 provides the individual potency-adjusted pharmacokinetic parameters of gaboxadol following single oral doses (2.5, 5, 10, 15, and 20 mg).

TABLE 1

Pharmacokinetic parameters for gaboxadol following oral and IV administration

Geometric Mean (N = 10)

| Parameter | 2.5 mg | 5 mg | 10 mg Oral | 10 mg I.V. | 15 mg | 20 mg | Slope (90% CI)[††] |
|---|---|---|---|---|---|---|---|
| $AUC_{0-\infty}$ (ng · hr/mL) | 90 | 171 | 346 | 380 | 539 | 669 | 0.98 (0.95, 1.01) |
| $C_{max}$ (ng/mL)[†] | 61 | 110 | 232 | 212 | 382 | 393 | 0.95 (0.88, 1.02) |
| $T_{max}$ (hr)[‡] | 0.5 | 0.6 | 0.5 | — | 0.5 | 0.6 | |
| Apparent $t_{1/2}$ (hr)[§] | 1.5 | 1.5 | 1.6 | 1.5 | 1.5 | 1.6 | |
| CL/F (mL/min)[ƻ] | 461 | 488 | 476 | 438 | 469 | 499 | |
| $f_c$ (%) | 43 | 45 | 53 | 53 | 50 | 53 | |
| $CL_R$ (mL/min) | 196 | 222 | 250 | 208 | 234 | 265 | |
| F (%) (90% CI)[§] | | | | 92% (0.86, 0.97) | | | |

[†]$C_{max}$ (ng/mL) for 10 mg I.V.
[‡]Median.
[§]Harmonic Mean.
[ƻ]CL (mL/min) for 10 mg I.V.
[#]Bioavailability relative to 10 mg I.V. reference based on pooled dose-adjusted (to 10 mg) oral $AUC_{0-\infty}$ values.
[††]Dose proportionality assessment of oral treatments only.

FIG. 1 shows the arithmetic mean plasma concentration-time profiles of gaboxadol following single oral doses (2.5, 5, 10, 15, and 20 mg). The bioavailability of gaboxadol is approximately 92%. Plasma $AUC_{0-\infty}$ and $C_{max}$ of gaboxadol show dose proportional increases and appear to be linear over the entire dose range examined, from of 2.5 to 20 mg. The time to peak plasma concentrations ($T_{max}$ 30-60 min) and the half-life (t½ of 1.5 h) for gaboxadol appear to be independent of dose across the gaboxadol dose range of 2.5 to 20 mg. The excretion of gaboxadol is mainly via urine, where 96.5% of the dose is recovered; 75% is recovered within 4 hours after administration.

Example 2

Assessment of Residual Effects Resulting from Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg.

All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit symbol substitution test (DSST), Tracking, Memory tests, Body Sway, and Leeds Sleep Evaluation Questionnaire).

Example 3

Study of Driving Performance after Gaboxadol Administration

This study was a double blind, randomized, placebo and active controlled 5 way cross over study to investigate the effect of evening and middle of the night dosing of gaboxadol on driving performance. The study participants included healthy, male and female subjects between 21 and 45 years of age, with a valid drivers license for at least 3 years.

The effects of gaboxadol on driving performance were investigated using real driving on the road setting. Subjects received 15 mg gaboxadol either in the evening prior to going to bed or at 4 am in the middle of the night following a wake-up call. Following a cognitive and psychomotor test battery, the driving test started at 9 am and lasted for one hour. Gaboxadol 15 mg had a clinically relevant impairing effect on driving following middle-of-the-night administration.

Following the evening dose, a statistically significant effect of gaboxadol 15 mg was observed on driving. However, this effect was less than the effect observed at a 0.05% blood alcohol concentration, the concentration limit at which driving is prohibited in most European countries. There was generally a numerically greater effect following zopiclone (7.5 mg) and zolpidem (10 mg) administered in the evening and in the middle of the night, respectively. Both the evening and the middle-of-the-night dose of gaboxadol were well tolerated with the most frequent adverse events being dizziness, nausea and somnolence for the middle-of-the-night treatment and headache and somnolence for the evening treatment.

Subjects on the active reference zopiclone had a numerically greater effect in the same test. There was no effect on memory test, body sway, DSST or critical tracking, whereas zopiclone had effect on several of these tests.

Example 4

Study of Daytime Performance after Sleep Restriction

This study was a 4-night, parallel-group, randomized, double-blind (with in-house blinding), placebo-controlled, fixed-dose study to assess the effects of gaboxadol on daytime performance in healthy adults subjected to a 5-hour sleep restriction. The study included a 2-night single-blind placebo run-in period, a 4-night double-blind treatment period during which sleep was restricted to 5 hours and a 2-night single-blind placebo run-out period. The study included healthy male and female volunteers 18 to <55 years of age.

2-night run-in period: All patients received placebo
4-night double-blind treatment period: Patients were randomized to gaboxadol 15 mg or matching placebo
2-night run-out period: All patients received placebo The primary endpoints included observations based on the Multiple Sleep Latency Test (MSLT) and Slow Wave Sleep (SWS) assessment. The primary objective was to evaluate the efficacy of gaboxadol (15 mg) compared to placebo in reducing daytime sleep propensity as measured by MSLT. The gaboxadol subjects had significantly less daytime sleepiness during the Sleep Restriction period than did placebo subjects (p=0.047, 1 sided). The MSLT was on average 2.01 minutes longer for subjects treated with gaboxadol (15 mg) than for those with placebo on the last two Sleep Restriction days.

In addition, a secondary objective was to evaluate the efficacy of gaboxadol compared to placebo in increasing the amount of slow wave sleep (SWS) during the last 2 nights of sleep restriction. Subjects receiving gaboxadol experienced significantly more SWS during the Sleep Restriction period than did placebo subjects (p<0.001, 1 sided). Moreover, subjects treated with gaboxadol on average had 20.53 minutes of SWS longer than those treated with placebo on the last two Sleep Restriction nights.

Finally, this study examined the efficacy of gaboxadol compared to placebo during the last 2 nights/days of sleep restriction in: (1) improving memory and attention as assessed by a neurobehavioral battery; (2) reducing subjective sleepiness as measured by the Karolinska Sleepiness Score (KSS); (3) altering sleep parameters (e.g., total sleep time, latency to onset of Slow Wave Sleep (SWS), slow wave activity (SWA); and (4) reducing biological stress typified by increased heart rate variability, and decreased cortisol levels and decreased catecholamine levels, as well as decreased body temperature.

There was a trend towards less subjective daytime sleepiness for the gaboxadol subjects during the Sleep Restriction period as compared with placebo subjects. The Karolinska Sleepiness Score (KSS) was on average 0.68 less for subjects treated with gaboxadol than for those treated with placebo on the last two Sleep Restriction days (p=0.058, 1 sided) as evaluated by a Longitudinal data analysis (LDA) model with adjustment for baseline KSS, gender, and age. A supportive analysis using covariance (ANCOVA) also supports this finding. The effect sizes computed for the neurocognitive battery showed that there was no strong evidence that gaboxadol improves daytime performance. There were no differences between gaboxadol and placebo with respect to biophysiological measures of stress (heart rate variability, cortisol levels, catecholamine levels, body temperature).

Compared with placebo, gaboxadol has a protective effect on reducing daytime sleepiness as measured by the MSLT on the last 2 days of 4-nights of sleep restriction. Compared with placebo, gaboxadol increases the amount of slow wave sleep (SWS) during the last 2 nights of 4-nights of sleep restriction.

Example 5

Prospective Assessment of the Efficacy of Gaboxadol in Patients with Dravet Syndrome This study is designed to determine whether gaboxadol leads to an improvement in one or more symptoms of Dravet syndrome. Individuals with Dravet syndrome may suffer from severe disruptions in sleep, impairments in speech, behavioral and developmental delays, movement and balance issues, delayed language and speech issues, growth and nutrition issues, chronic infections, sisruptions of the autonomic nervous system and frequent seizures with characteristic abnormal electroencephalogram (EEG) patterns. All main domains of symptoms of Dravet syndrome (e.g., seizure activity, sleep, gross and fine motor function, behavior and communication) will be investigated, using appropriate questionnaires, diaries or actimetric data. Main focus may include seizure activity, motor ability and sleep. Well-established scales may be used, complemented by more innovative outcome measures for sleep and motor function. A potential confounding factor for behavior in Dravet syndrome is the co-existence of autism. At Screening, subjects may be assessed for this co-morbidity, using the Autism Diagnostic Observation Schedule (ADOS), and potentially excluded.

The primary objective of this study may be to evaluate the safety and tolerability from Baseline to Week 6 and Week 12 of gaboxadol in adult subjects with Dravet syndrome across different dose levels and in two dosing schedules. The following dosing schedules may be tested against placebo: (1) Once daily (o.d.): An evening dose, titrated to the target dose of 15 mg unless not tolerated; and (2) Twice daily (b.i.d.): Evening and morning doses titrated to the target doses of 15 mg evening dose and 10 mg morning dose unless not tolerated.

The Safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine); (4) Suicidality assessed by ABC-Irritability Subscale; (5) EEG (change in background frequency, intensity of epileptiform discharges); and/or (6) Caregivers may maintain an electronic seizure diary (on same device as sleep log).

The secondary objective of this study may include the identification of a set of parameters that may best characterize the efficacy of gaboxadol in adult Dravet syndrome subjects for subsequent efficacy trials. These tests may be administered at four full day site visits (Screening, Baseline, Interim and End of Treatment) by an appropriately trained professional to provide the test to an adult Dravet syndrome patient. Assessments may be based on direct observation and input from caregivers. The efficacy assessments that may be explored include Gross Motor Ability/Function and Fine Motor Ability/Function. Evaluation of Gross Motor Ability/Function may include analysis of spatiotemporal and functional gait measurements (Zeno Walkway and PKMAS software analysis, provided by ProtoKintetics) and Modified Performance Oriented Mobility Assessment-Gait (MPOMA-G) scale assessed while subject is walking on Zeno Walkway.

Evaluation of Fine Motor Ability/Function may include analysis of Pediatric Evaluation of Disability Inventory (PEDI-CAT); ADL (to document fine motor function) and mobility domains in the content-balanced (more extensive) version.

Evaluation of sleep may include analysis by actigraphy to measure: (1) Sleep Onset Latency (SOL); (2) Total Sleep Time (TST); (3) Wake After Sleep Onset (WASO)=total # of wake epochs after sleep onset; (4) Nocturnal Awakenings (NA); and/or (5) Sleep Efficiency=total sleep time (TST) of time in bed (TIB). Additional evaluation of sleep may include analysis of parent/caregiver logs of sleep patterns that may include: (1) bed time; (2) time of sleep onset; (3) number and duration of awakenings; (4) number of disruptive behavior; (5) time of last awakening; and (6) daytime sleepiness.

Evaluation of seizure activity may include EEG monitoring (change in background frequency, intensity of epileptiform discharges).

This study may include three treatment groups. For example, a total of approximately 75 subjects may be enrolled and at the completion of the study, there may be approximately 25 subjects in each of the three treatment groups: 1) single evening dose 2) morning and evening dose and 3) placebo.

Figure 2:
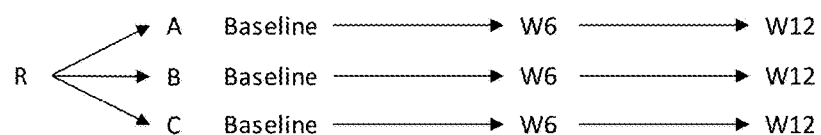
FIG. 2 is a schematic depiction of three dosing schedules (A, B and C) in connection with a prospective assessment of the efficacy of gaboxadol in patients with Dravet syndrome according to Example 5.

All subjects may receive a morning dose (either active or placebo) and an evening dose (either active or placebo) during the entire duration of treatment. For example, as shown schematically in FIG. 2, two dosing schedules of gaboxadol may be tested: a single evening dose (o.d.; Schedule A) and a morning plus evening dose (b.i.d; Schedule B) designed to provide a more sustained exposure. Schedule C is morning and evening placebo. All subjects may be up-titrated to the target dose unless this target dose is not tolerated (titration conventions described below). All subjects may receive treatment for a maximum of 12 weeks at their optimal tolerated dose.

Figure 3:
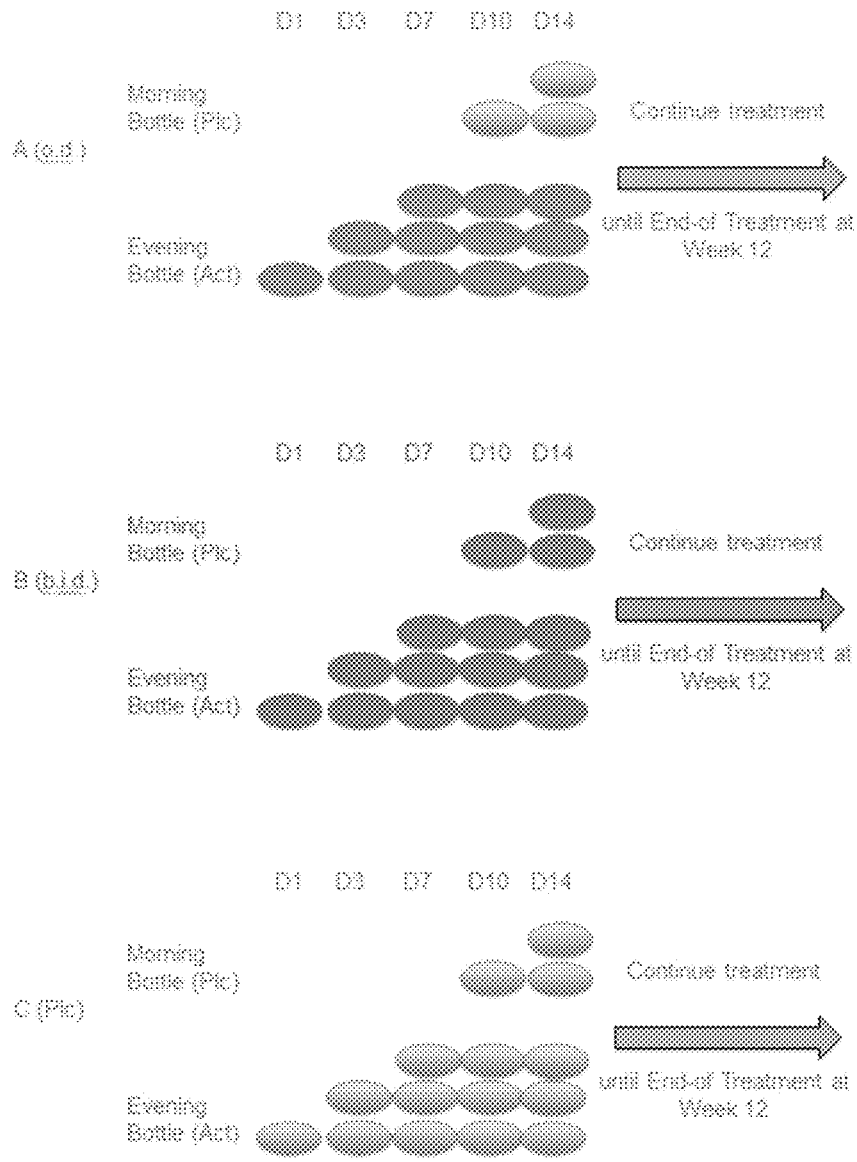
FIG. 3 is a graphic depiction of the three dosing schedules depicted in FIG. 2. Solid gray ovals indicate active ingredient containing dosage forms. Partial gray ovals indicate placebos.

Doses may be progressively increased in 5 mg increments (active or placebo) to a target dose of 3 capsules evening dose in schedule A and B, and 2 capsules morning dose in schedule B. Each dose escalation may be performed after adequate tolerability will be assessed by caregiver and investigator. For example, as shown graphically in FIG. 3, treatment initiation at Day 1 with 1 capsule (active or placebo) in the evening. Then Target up-titration may begin at Day 3 (window+2 days): If no adverse event (AE) related to the study drug is observed by caregiver and/or the investigator, another capsule (active or placebo) is added in the evening. Again at Day 7 (window+2 days), Day 10 (window+2 days and Day 14 (window+2 days) if no AE related to the study drug is observed by caregiver and/or the investigator, another capsule (active or placebo) may be added in the morning.

Slowed up-titration or delayed up-titration will be acceptable if tolerability does not allow immediate further dose-escalation at any of the above detailed days (3, 7, 10, 14). Down-titration in the case tolerability is not acceptable (e.g., somnolence, dizziness, change in behavior) after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (2 capsules in the morning and 3 in the evening) the subject may be kept stable until End of Treatment visit (week 12) unless intolerability requires down-titration.

All subjects will be screened for participation in the study up to 28 days prior to the first dose administration. Inclusion criteria may include one or more of the following: (1) Age≥18 years, ≤40 years; (2) Must possess a clinical diagnosis of Dravet syndrome according to the consensus criteria with developmental delay, movement or balance disorder, and speech disorder; (3) Must possess a previous or current molecular confirmation of Dravet syndrome; (4) Subjects must be receiving a stable dose of concomitant medications, including anti-epileptic medication, supplements, and special diets, for at least 4 weeks prior to Baseline, and be able to maintain these throughout the duration of the study.

Exclusion Criteria may include one or more of the following: (1) Non-ambulatory subjects (e.g. requiring a wheelchair) not able to perform the tests for Assessment of Motor Ability/Function (as described above); (2) Poorly controlled seizures defined as >3 absence-type seizure per week and/or >1 major seizure episodes per month; (3) Concomitant cardiovascular, respiratory diseases; Concomitant liver disease with alanine aminotransferase or aspartate aminotransferase >2.5×upper limit of normal (ULN); (4) Concomitant renal disease with creatinine above ULN (5) Concomitant hematologic disease with absolute neutrophil count >2×$10^9$/L or platelets <50×$10^9$/L or hemoglobin <80 g/L; (6) Other genetic disorders; (7) Concomitant use of minocycline, levodopa, sleep medication and any other use of any investigational agent, device, and/or investigational procedure 4 weeks prior to Baseline and during the study; (8) At risk of suicide based on ABC-Irritability Subscale Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Example 6

Prospective Assessment of the Efficacy of Gaboxadol in Patients with Dravet Syndrome This study is designed to determine whether lower doses of gaboxadol lead to an improvement in younger patients or patients with less severe clinically evaluated symptoms. For example, adolescent patients (age 12-18 years) may have the similar clinical presentation and baseline disease characteristics as the adult population but the reduction in ambulation may be less severe. In these patients it is anticipated that the target benefit of gaboxadol may also include the reduction in seizures, ataxia and the improvement in ambulatory function.

In pediatric patients (6 months to 12 years) the diagnosis of Dravet syndrome is usually made around 1 to 2 years of age based on important delay in the development status and eventually persistent seizures. As the child grows older, additional neurologic deficit will contribute to the disease presentation. For these prospective participants, the inclusion criteria for randomization and assessment procedures is similar to that previously described.

After randomization the participants are placed into 6 separate treatment groups (A-F) and a placebo group. Treatment group A receives 7.5 mg gaboxadol in the evening. Treatment group B receives 5 mg gaboxadol in the evening. Treatment group C receives 5 mg gaboxadol in the evening and 2.5 mg gaboxadol in the morning. Treatment group D receives 2.5 mg gaboxadol in the evening. Treatment group E receives 2.5 mg gaboxadol in the evening and 1 mg gaboxadol in the morning. Treatment group F receives 1 mg gaboxadol in the evening.

Those skilled in the art will recognize, or be able to ascertain using no more than routine experimentation, many equivalents to the specific embodiments described herein. Such equivalents are intended to be encompassed by the claims.

What is claimed is:

1. A method of treating Dravet syndrome comprising administering to a patient in need thereof a pharmaceutical composition comprising 0.1 mg to 50 mg gaboxadol or a pharmaceutically acceptable salt thereof.

2. The method of claim 1 wherein the composition provides reduction in the frequency of seizures, the severity of seizures, or a combination thereof in a patient diagnosed with Dravet syndrome.

3. The method of claim 1 wherein gaboxadol or a pharmaceutically acceptable salt thereof is administered to the patient in a daily dosage ranging from 1 mg to 50 mg.

4. The method of claim 1 wherein the pharmaceutical composition comprises 2.5 mg to 30 mg gaboxadol.

5. The method of claim 1 wherein gaboxadol or a pharmaceutically acceptable salt thereof is administered in a dose ranging from 0.1 mg/kg to 1 mg/kg.

6. The method of claim 1 wherein the composition is administered once, twice, three times daily, or every other day.

7. The method of claim 1 further comprising administering a compound selected from the group consisting of pipradrol, acetazolamide, carbamazepine, clobazam, clonazepam, eslicarbazepine acetate, ethosuximide, gabapentin, lacosamide, lamotrigine, leviteracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

* * * * *